United States Patent
Thomas

(10) Patent No.: US 10,993,653 B1
(45) Date of Patent: May 4, 2021

(54) MACHINE LEARNING BASED NON-INVASIVE DIAGNOSIS OF THYROID DISEASE

(71) Applicant: Johnson Thomas, Springfield, MO (US)

(72) Inventor: Johnson Thomas, Springfield, MO (US)

(*) Notice: Subject to any disclaimer, the term of this patent is extended or adjusted under 35 U.S.C. 154(b) by 9 days.

(21) Appl. No.: 16/505,622

(22) Filed: Jul. 8, 2019

Related U.S. Application Data

(60) Provisional application No. 62/697,403, filed on Jul. 13, 2018.

(51) Int. Cl.
*G06K 9/00* (2006.01)
*A61B 5/00* (2006.01)
(Continued)

(52) U.S. Cl.
CPC .......... *A61B 5/4227* (2013.01); *A61B 5/0095* (2013.01); *A61B 8/085* (2013.01);
(Continued)

(58) Field of Classification Search
CPC ......... G06T 7/0012; G06T 2207/10081; G06T 2207/30061; G06T 2207/30064; G06T 7/11; G06T 5/30; G06T 7/12; G06T 7/155; G06T 2200/04; G06T 2207/10116; G06T 5/002; G06T 2207/10072; G06T 7/62; G06T 11/008; G06T 2207/20081;
(Continued)

(56) References Cited

U.S. PATENT DOCUMENTS

| | | | |
|---|---|---|---|
| 2002/0186875 A1 | 12/2002 | Burmer et al. | |
| 2004/0086161 A1* | 5/2004 | Sivaramakrishna | .. G06T 7/0012 382/131 |
| 2012/0220875 A1 | 8/2012 | Suri | |

FOREIGN PATENT DOCUMENTS

| | | |
|---|---|---|
| CN | 106056595 A | 10/2016 |
| CN | 106780448 A | 5/2017 |

(Continued)

OTHER PUBLICATIONS

Ma, Ultrasound image-based thyroid nodule automatic segmentation using convolutional neural network, Jul. 2017 (Year: 2017).*

(Continued)

*Primary Examiner* — Alex Kok S Liew

(57) ABSTRACT

A system includes a computing device that receives a query thyroid image, where the query thyroid image is an ultrasound image of a thyroid comprising a thyroid nodule of interest. The computing device processes the query thyroid nodule image using a machine learning model to identify at least one labelled thyroid image from a plurality of labelled thyroid images that is similar to the query thyroid nodule image. The plurality of labelled thyroid images are used as training data to generate the machine learning model. The at least one labelled thyroid image has labels associated therewith and comprises an ultrasound image of a thyroid nodule that has a confirmed diagnosis. The computing device generates an output report based on the labels associated with the at least one labelled thyroid image, where the output report indicates whether the thyroid nodule of interest resembles a malignant thyroid nodule or benign thyroid nodule.

18 Claims, 12 Drawing Sheets

(51) Int. Cl.
*A61B 8/08* (2006.01)
*G06T 7/00* (2017.01)

(52) U.S. Cl.
CPC .............. *A61B 8/48* (2013.01); *A61B 5/004* (2013.01); *G06T 7/0012* (2013.01)

(58) Field of Classification Search
CPC .......... G06T 2207/30096; G06T 5/005; G06T 15/08; G06T 17/10; G06T 2207/30068; G06T 7/136; G06F 19/321; G06K 2209/05; G06K 2209/051; G06K 2209/053; G06K 9/0014; G06K 9/6228; G06K 9/6229; G06K 9/6267; G06N 3/126; G06N 20/00
See application file for complete search history.

(56) References Cited

FOREIGN PATENT DOCUMENTS

| | | |
|---|---|---|
| CN | 106951928 A | 7/2017 |
| CN | 107247971 A | 10/2017 |
| CN | 107451615 A | 12/2017 |
| CN | 107680678 A | 2/2018 |
| CN | 105427296 B | 4/2018 |
| CN | 108171694 A | 6/2018 |
| KR | 101656582 B1 | 9/2016 |

OTHER PUBLICATIONS

Ma, A pre-trained convolutional neural network based method for thyroid nodule diagnosis, Sep. 2016 (Year: 2016).*

Tsantis, Development of a Support Vector Machine-Based Image Analysis System for Assessing the Thyroid Nodule Malignancy Risk on Ultrasound, Jul. 2005 (Year: 2005).*

Huang, "Deep Networks with Stochastic Depth," Jul. 2016 (Year: 2016).*

\* cited by examiner

MACHINE LEARNING BASED NON-INVASIVE DIAGNOSIS OF THYROID DISEASE

CROSS-REFERENCE TO RELATED APPLICATIONS

This application claims priority to U.S. Provisional Application No. 62/697,403 titled "Methods for diagnosing thyroid disease," and filed on Jul. 13, 2018 in the name of Johnson Thomas, the entire content of said application being incorporated herein by reference.

TECHNICAL FIELD

The present disclosure relates generally to the field of artificial intelligence based medical diagnostics; and more particularly to machine learning based non-invasive diagnosis of thyroid disease.

BACKGROUND

About 50-60% of women over the age of 50 have thyroid nodules, but only about 5% of the thyroid nodules are cancerous. Existing technology to determine whether a thyroid nodule is cancerous may include invasive procedures. One such invasive procedure includes thyroid biopsy to determine whether a thyroid nodule is cancerous. The number of thyroid biopsies done in United States alone has been increasing on a yearly basis. However, in many cases, biopsy may not provide definitive results. That is, the biopsy result may be inconclusive (e.g., indeterminate or inadequate), in which case, a repeat biopsy and/or a molecular diagnostic work up such as genetic testing may be done. In some cases, even the repeat biopsy and/or genetic testing may not be definitive. For example, there are certain mutations such as RAS mutations which affect the accuracy of such genetic testing because they appear in both benign thyroid nodules and cancerous thyroid nodules. In some cases, when the biopsy result is inconclusive, other invasive procedures such as thyroid surgery may be done. The additional and/or repeat invasive procedures may be cost-intensive and adds more expense to the care of the patient. Further, invasive procedures such as thyroid surgery involves risk and associated complications such as bleeding, injury to nerves causing hoarseness, injury to parathyroid gland causing low calcium and related side effects.

As described above, studies have shown that typically only about 5% of the thyroid nodules are cancerous; and only about a third of thyroid surgeries done for suspected cancer result in the actual diagnosis of cancer. So, it is highly undesirable that currently patients have to undergo risky invasive procedures such as thyroid surgery to diagnose thyroid cancer with 5% prevalence among detected thyroid nodules and a 98.1% 5-year survival rate.

Technologies that use non-invasive procedures to detect cancerous thyroid nodules do exist. One such non-invasive procedure includes visually analyzing an ultrasound image of a thyroid nodule to determine whether a thyroid nodule is cancerous based on guidelines provided by various medical professional organizations and international medical societies such as American and European thyroid associations and/or Radiology associations. However, the process of visually analyzing ultrasound images of the thyroid nodules to identify cancerous thyroid nodules may be subjective and is not definitive. That is, the results of such visual analysis may vary from one radiologist or physician to another. In most cases, the indefinite and subjective nature of the visual analysis eventually forces the physicians to revert to the invasive procedure in hopes of a definitive result.

Some existing non-invasive technologies perform a computer based classification of the ultrasound images of thyroid nodules using image classification algorithms. The image classification algorithms may be configured to classify the thyroid nodules based on the guidelines provided by medical associations and deep learning techniques. While the computer based classification technology may be objective, it has been found that the existing computer based classification technologies produce many false negative results. For example, the existing computer based classification technology may identify a thyroid nodule as being benign, but a subsequent biopsy may indicate that the thyroid nodule is cancerous. Current systems are also prone to false positives. Unlike other type of cancers, such as breast cancer, the proportion of benign looking nodules in thyroid is comparatively higher, thereby significantly increasing the chances of obtaining false negative classifications using the existing computer based image classification technology. Further, image classification technology is not configured to distinguish or identify fine-grained image similarities between images. Also, existing image classification technology operates as black boxes which are not transparent. That is, said existing image classification technologies do not explain to a physician why the nodules are classified benign or cancerous.

It is noted that this background information is provided to reveal information believed by the applicant to be of possible relevance to the present disclosure. No admission is necessarily intended, nor should be construed, that any of the preceding information constitutes prior art against the present disclosure.

SUMMARY

In one aspect, the present disclosure relates to a system that includes a computing device. The computing device includes an ultrasound imaging apparatus that is configured to capture an ultrasound image of a thyroid comprising a thyroid nodule of interest. Further, the system may include an analysis engine. The analysis engine is configured to generate, using a machine learning algorithm and a training dataset, a machine learning model that is configured to determine at least one labelled thyroid image that is similar to an ultrasound image of the thyroid nodule of interest. The training dataset comprises a plurality of labelled thyroid images, and wherein each labelled thyroid image comprises an ultrasound image of a thyroid nodule that has a confirmed diagnosis. Further, the analysis engine is configured to receive the ultrasound image of the thyroid captured by the ultrasound imaging apparatus. Furthermore, the analysis engine is configured to segment the ultrasound image of the thyroid to generate the ultrasound image of the thyroid nodule of interest, and process, using the machine learning model, the ultrasound image of the thyroid nodule of interest to determine the at least one labelled thyroid image from the plurality of labelled thyroid images that is similar to the ultrasound image of the thyroid nodule of interest. Additionally, the analysis engine is configured to determine, based on the at least one labelled thyroid image, whether the thyroid nodule of interest is one of the malignant thyroid nodule and the benign thyroid nodule.

In another aspect, the present disclosure is related to a non-transitory computer-readable medium comprising a plurality of instructions, which, when executed by an analysis engine of a computing device, causes the computing device to perform operations. The operations include generating, using a machine learning algorithm and a training dataset, a machine learning model that is configured to determine at least one labelled thyroid image that is similar to an ultrasound image of a thyroid nodule of interest. The training dataset comprises a plurality of labelled thyroid images, and wherein each labelled thyroid image comprises an ultrasound image of a thyroid nodule that has a confirmed diagnosis. Further, the operations include receiving an ultrasound image of a thyroid comprising the thyroid nodule of interest, segmenting the ultrasound image of the thyroid to generate the ultrasound image of the thyroid nodule of interest, and processing, using the machine learning model, the ultrasound image of the thyroid nodule of interest to determine the at least one labelled thyroid image from the plurality of labelled thyroid images, the at least one labelled thyroid image being similar to the ultrasound image of the thyroid nodule of interest. Furthermore, the operations include determining, based on the at least one labelled thyroid image, whether the thyroid nodule of interest is one of a malignant thyroid nodule and a benign thyroid nodule.

In yet another aspect, the present disclosure relates to a computing device. The computing device includes an analysis engine that is configured to determine whether a thyroid nodule of interest is one a malignant thyroid nodule and a benign thyroid nodule. The analysis engine includes a model generation module that generates, using a machine learning algorithm and a training dataset, a machine learning model that is configured to determine at least one labelled thyroid image that is similar to an ultrasound image of the thyroid nodule of interest. The training dataset comprises a plurality of labelled thyroid images, and wherein each labelled thyroid image comprises an ultrasound image of a thyroid nodule that has a confirmed diagnosis. The analysis engine further includes an image processing module that receives an ultrasound image of a thyroid comprising the thyroid nodule of interest; and segments the ultrasound image of the thyroid to generate the ultrasound image of the thyroid nodule of interest. Furthermore, the analysis engine includes a model application module that processes, using the machine learning model, the ultrasound image of the thyroid nodule of interest to determine the at least one labelled thyroid image from the plurality of labelled thyroid images, the at least one labelled thyroid image being similar to the ultrasound image of the thyroid nodule of interest. Additionally, the analysis engine includes an output generation module that determines, based on the at least one labelled thyroid image, whether the thyroid nodule of interest is one of a malignant thyroid nodule and a benign thyroid nodule.

These and other aspects, objects, features, and embodiments, will be apparent from the following description and the appended claims.

BRIEF DESCRIPTION OF THE FIGURES

The foregoing and other features and aspects of the disclosure are best understood with reference to the following description of certain example embodiments, when read in conjunction with the accompanying drawings, wherein.

Figure 1:
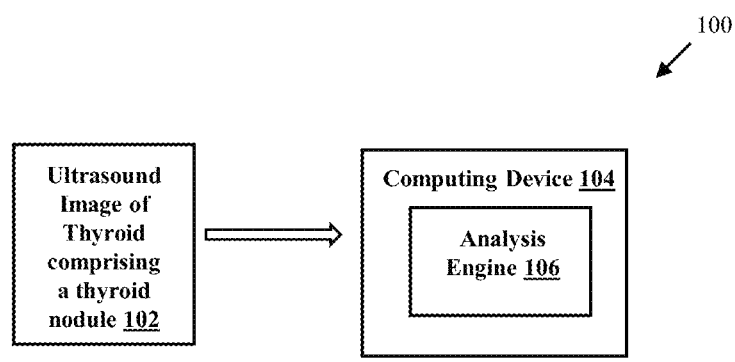
FIG. 1 illustrates an example operating environment of a thyroid nodule diagnosis system, in accordance with example embodiments of the present disclosure.

The drawings illustrate only example embodiments of the disclosure and are therefore not to be considered limiting of its scope, as the disclosure may admit to other equally effective embodiments. The elements and features shown in the drawings are not necessarily to scale, emphasis is instead placed on clearly illustrating the principles of the example embodiments. Additionally, certain dimensions or positioning may be exaggerated to help visually convey such principles.

DETAILED DESCRIPTION OF EXAMPLE EMBODIMENTS

The present disclosure describes a system, apparatus, and method for machine learning based non-invasive diagnosis of thyroid disease (hereinafter 'non-invasive diagnostic system'). In the description, well known components, methods, and/or processing techniques are omitted or are briefly described so as not to obscure the disclosure. As used herein, the "present disclosure" refers to any one of the embodiments of the disclosure described herein and any equivalents. Furthermore, reference to various feature(s) of the "present disclosure" is not to suggest that all embodiments must include the referenced feature(s).

The example non-invasive diagnostic system of the present disclosure uses a combination of artificial neural network technology, image similarity technology, and ultrasound imaging technology for a specific application of identifying malignant and benign thyroid nodules with minimal false negatives or false positives. In one example, the example non-invasive diagnostic system of the present disclosure includes a thyroid nodule analysis engine (hereinafter 'analysis engine'). The analysis engine may be configured to receive an ultrasound image of a thyroid that comprises a thyroid nodule of interest (hereinafter 'query thyroid image') and process, using an image similarity machine learning model (hereinafter interchangeable referred to as 'machine learning model' or 'thyroid diagnostics model'), the query thyroid image to identify whether the thyroid nodule of interest in the query thyroid image is malignant or benign.

The machine learning model may be configured to generate feature vectors associated with the query thyroid image and use the feature vectors to identify at least one labelled thyroid image that is similar to the query thyroid image. The labelled thyroid image may be stored in a training dataset database comprising a plurality of labelled thyroid images, where each labelled thyroid image comprises an ultrasound image of a thyroid nodule that has one or more labels associated therewith. The one or more labels may be representative of data (e.g., diagnosis data, other clinically useful data, genetic mutation data, etc.) associated with the thyroid nodule that has been confirmed based on cytopathology, surgical pathology, molecular testing results, etc.

Responsive to identifying the at least one labelled thyroid image that is similar to the query thyroid image, the analysis engine may be configured to generate and display an output report based on the one or more labels associated with the at least one labelled thyroid image that is similar to the query thyroid image. In particular, the output report may indicate whether the thyroid nodule of interest in the query thyroid image is malignant or benign based on the one or more labels associated with at least one labelled thyroid image that is similar to the query thyroid image. For example, if the one or more labels associated with at least one labelled thyroid image indicate that the thyroid nodule of the labelled thyroid image is a malignant thyroid nodule, then the thyroid nodule of interest is determined to be malignant.

In some examples, in addition to indicating whether the thyroid nodule of interest is benign or malignant, the analysis engine may be configured to provide additional data associated with the thyroid nodule of interest in the output report, where the additional data further defines the thyroid nodule of interest and/or provides treatment options, potential interventions, etc. Such additional data associated with the thyroid nodule of interest may be provided based on one or more labels associated with at least one labelled thyroid image that is similar to the query thyroid image, other available medical information and corpus of medical knowledge associated with thyroid diseases.

Further, in some examples, the analysis engine may be configured to protect patient information. For example, all patient information associated with the query thyroid image may be removed before processing the query thyroid image using the machine learning model to determine whether the thyroid nodule of interest in the query thyroid nodule is benign or malignant. The patient information that is removed may be stored in a secure database and associated with a unique identifier that is provided to the query ultrasound image by the analysis engine. Only authorized users may be provided access to the patient information in the secure database.

The deep learning model may be created by training a machine learning algorithms using the plurality of labelled thyroid images in the training dataset database. The machine learning algorithm may be a multi-layer neural network algorithm such as a convolutional neural network algorithm that has been modified to recognize visual patterns in an input image and use said visual pattern to find other labelled images that are similar to an input image. Existing convolution neural networks models are typically configured for general image classification. So, existing convolutional neural networks have to be modified for the intended purpose of the present disclosure, i.e., to find labelled images of thyroid nodules that are similar to query thyroid nodule that comprises a thyroid nodule of interest.

The non-invasive diagnostic system of the present disclosure provides a safe, non-invasive, objective, and cost-effective method to identify thyroid nodules with significantly lower false negative results. This in turn reduces the number of inconclusive results and the number of invasive procedures such as thyroid biopsy and surgery that need to be performed. One unexpected result that was achieved using the non-invasive diagnostic system of the present disclosure was the positive identification of specific types of thyroid cancers such as follicular thyroid cancer, follicular variant of papillary thyroid cancer, and hurthle cell thyroid cancer that may have been misclassified as being benign using current classification systems. Further, the non-invasive diagnostic system of the present disclosure is configured to: (a) provide an easy plug and play option and/or (b) retrofit existing medical equipment, which in turn allows easy installation, allows universal use, and eliminates the need to use bulky equipment that may not be portable, may consume lots of space, and may be cost-prohibitive. Furthermore, the non-invasive diagnostic system of the present disclosure is configured to operate within the strict privacy policies in the medical field such as HIPAA laws. For example, the non-invasive diagnostic system of the present disclosure is configured to protect patient information. For example, the non-invasive diagnostic system may remove patient information from the query thyroid image before transmitting it for processing, store the patient information in a secure database, and provide access to the patient information only to authorized users. In one of the embodiments, the present invention can be deployed on a local machine, hence the data will not go out of the medical facility.

The non-invasive diagnostic system of the present disclosure will be further described in greater detail below. However, before discussing the example embodiments directed to the non-invasive diagnostic system, it may assist the reader to understand the various terms used herein by way of a general description of the terms in the following paragraphs.

The term 'machine learning' as used herein generally refers to a type of artificial intelligence (AI) that provides computers with the ability to learn without being explicitly programmed. Machine learning focuses on the development of computer programs that can teach themselves to grow and change when exposed to new data.

The term 'machine learning model' as used herein generally refers to a mathematical representation of a real-world process that is created by training a machine learning algorithm using a training data. Unless specified otherwise, the term machine learning model as used herein may refer to an image similarity machine learning model (also referred to as thyroid diagnostics model).

The term 'feature vector' as used herein generally refers to an n-dimensional vector of numerical features that represent an object such as a thyroid nodule in an ultrasound image of a thyroid comprising the thyroid nodule.

The term 'similar' as used herein in the context of similarity between ultrasound images may generally refer to an exact match between the ultrasound images and/or ultrasound images that closely resemble each other without being identical (e.g., having substantially similar features without being identical).

The term 'thyroid nodule of interest' as used herein may generally refer to a thyroid nodule that needs to be diagnosed using the non-invasive system described herein.

It will be appreciated that the various embodiments discussed herein need not necessarily belong to the same group of exemplary embodiments and may be grouped into various other embodiments not explicitly disclosed herein. In the following description, for purposes of explanation, numerous specific details are set forth in order to provide a thorough understanding of the various embodiments.

Technology associated with the non-invasive diagnostic system will now be described in greater detail with reference to FIGS. 1-12. In particular, first, FIGS. 1-4 will be discussed in the context of describing representative operating environments associated with the non-invasive diagnostic system, according to certain exemplary embodiments of the present invention. Further, FIGS. 5-12 will be discussed, making exemplary reference back to FIGS. 1-3 as may be appropriate or helpful.

Referring to FIG. 1, in one example embodiment, the non-invasive diagnostic system 100 may include a computing device 104 that comprises an analysis engine 106 disposed or installed therein. The computing device 104 may be configured to receive a query thyroid image 102 (i.e., ultrasound image of a thyroid that comprises a thyroid nodule of interest).

The computing device 104 may receive the query thyroid image 102 from an appropriate source via wireless and/or wired communication. For example, the computing device 104 may receive the query thyroid image 102 directly from an ultrasound imaging machine, a medical imaging database, a picture archiving and communication system (PACS), etc., that is communicatively coupled to the computing device 104. In another example, the computing device 104 may receive the query thyroid image 102 from a portable storage device such as USB stick that has the query thyroid image 102 stored therein. If the portable storage device comprises wireless communication capability such as a Wi-Fi enabled USB stick, the query thyroid image 102 stored therein may be wirelessly transferred to the computing device 104. Alternatively, the portable storage device may be physically connected to the computing device 104 to transfer the query thyroid image 102 thereto. The examples provided above for transferring the query thyroid image 102 to the computing device 104 may be non-limiting. That is, one of skill in the art can understand and appreciate that the computing device 104 may be configured to receive the query thyroid image 102 through any other appropriate data transfer methods without departing from a broader scope of the present disclosure, provided that the data transfer method does not violate patient privacy and/or the medical data transfer regulations (e.g., HIPAA (Health Insurance Portability and Accountability Act) laws and regulations). In some examples, the query thyroid image 102 received at the computing device 104 may not include any private or sensitive data associated with the patient. That is, all (or at least private or sensitive) patient data associated with the query thyroid image 102 may be removed therefrom by a source thereof before the query thyroid image 102 is transmitted to the computing device 104. In said example embodiments, the query thyroid image 102 may include a unique identifier that may be used to identify the query thyroid image 102 and later retrieve patient information (by authorized users).

Figure 2:
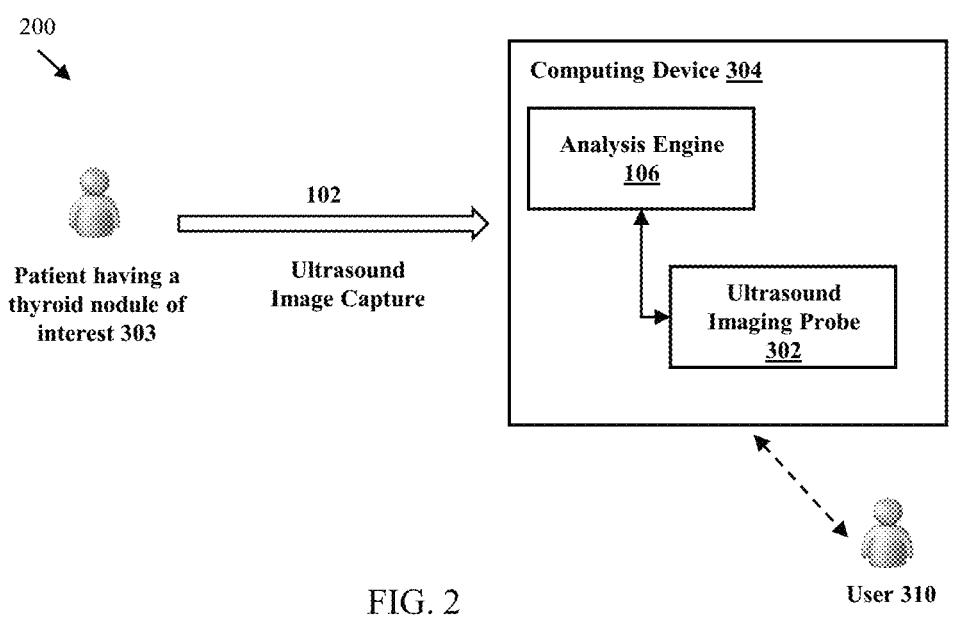
FIG. 2 illustrates another example operating environment of the thyroid nodule diagnosis system, in accordance with example embodiments of the present disclosure.

In another example embodiment, as illustrated in FIG. 2, the non-invasive diagnostic system 200 may include a computing device 304 that comprises the analysis engine 106 and an ultrasound imaging probe 302 that is communicatively coupled to the analysis engine 106. In one example, the ultrasound imaging probe 302 may be configured to be removably coupled to the computing device 304. Alternatively, in another example, the ultrasound imaging probe 302 may be integrated with the computing device 304. In the example embodiment of FIG. 2, instead of receiving the query thyroid image 102 from an external source as described above in association with FIG. 1, the computing device 304 may be configured to directly capture the query thyroid image 102 associated with a patient 303 using the ultrasound imagine probe 302. In other words, a user 310 such as a physician or an ultrasound technician may use the ultrasound imaging probe 302 and interact with the computing device 304 to capture the query thyroid image 102 of the patient 303.

In either case, i.e., whether the query thyroid image 102 is received from an external source or captured by an ultrasound imagine probe 302 of a computing device (e.g., computing device 304), responsive to receiving the query thyroid image 102, the query thyroid image 102 may be segmented to generate an ultrasound image of an area of interest (e.g., an ultrasound image of the thyroid nodule of interest) (hereinafter 'query thyroid nodule image'). In one example, the analysis engine 106 of the computing device (104, 304) may be configured to segment the query thyroid image 102 to generate the query thyroid nodule image. However, in another example, the query thyroid image 102 may be manually segmented using the computing device (104, 304). Responsive to generating the query thyroid nodule image, the analysis engine 106 may be configured to process, using a machine learning model, the query thyroid nodule image to determine whether the thyroid nodule of interest in the query thyroid nodule image is malignant or benign based on machine learning technology and/or image similarity technology. Furthermore, the analysis engine 106 may be configured to provide additional information regarding the thyroid nodule of interest. The machine learning model may be generated by a machine learning algorithm as an initial set-up prior to receiving the query thyroid image 102.

Figure 12:
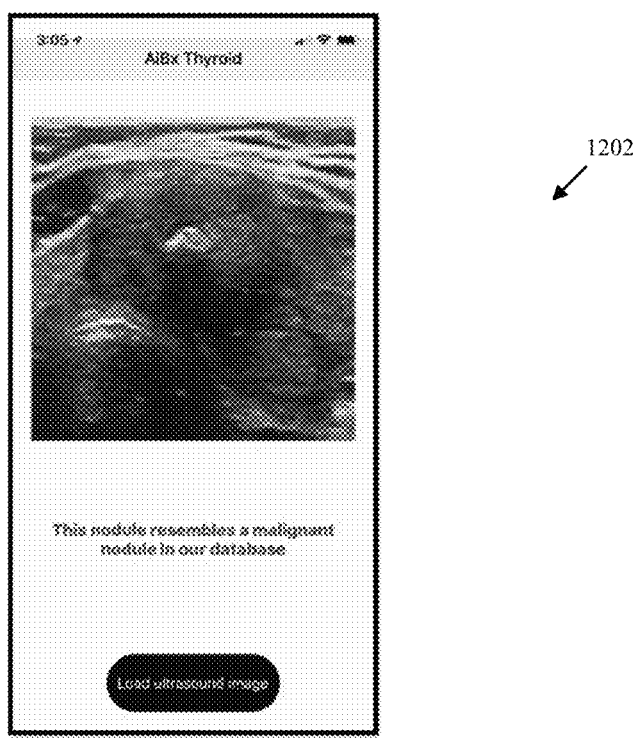
FIG. 12 illustrates an example visual output of the thyroid nodule diagnosis system, in accordance with example embodiments of the present disclosure.

Additionally, the analysis engine 106 may be configured to generate an output report that: (a) indicates whether the thyroid nodule of interest in the query thyroid image 102 is benign or malignant and/or (b) provides additional information associated with the thyroid nodule of interest. The analysis engine 106 may be configured to present the output report via a display 510 (shown in FIGS. 5 and 6) of the computing device (104, 304). One such non-limiting example output report 1202 that is presented via a display of a smart phone is illustrated in FIG. 12.

In some example embodiments, the analysis engine 106 may provide an option (or prompt a user) to verify the data presented in the output report 1202. A user may interact with the computing device (104, 304) to verify the output report 1202. If the user informs that the data presented in the output report 1202 (e.g., data associated with the thyroid nodule of interest) is inaccurate, then, the query thyroid image 102 may be marked as an exception. For example, if the analysis engine 106 determines that a thyroid nodule of interest in the query thyroid image 102 is benign and later if said determination is deemed as being incorrect by a user such as a physician or a radiologist; then the query thyroid image 102 is marked as an exception. Further, the query thyroid image 102 marked as exception may either be stored in a database for future reference or provided as feedback to further train and optimize the machine learning model. In some embodiments, even if the user verifies the data presented in the output report 1202 as being accurate, the corresponding query thyroid image 102 may be provided as feedback to optimize the machine learning model.

In some example embodiments, the query thyroid image 102 that is received at or captured by the computing device (104, 304) may include the patient data. In said example embodiment, the computing device (104, 304) may save or store the query thyroid image 102 in a memory 506 of the computing device (104, 304) for processing or analyzing the query thyroid image 102 later or for future reference. However, prior to storing the query thyroid image 102 in the memory 506, the computing device (104, 304) may be configured to remove patient data associated with the query thyroid image 102 (or any appropriate data and/or metadata associated with the ultrasound image that would cause HIPAA violation). The removed patient data may be stored in a secure database in the computing device 104. Removal of the patient data associated with the ultrasound image of the thyroid 102 may include, but is not limited to, electronic/digital scrubbing, redaction, removing metadata representative of patient data, etc. Further, the query thyroid image 102 from which the patient data has been removed may be assigned a unique identifier. The unique identifier may be stored in the secure database and associated with the patient data that is removed from the query thyroid image 102. The secure database may only be accessed by authorized users, such as a physician treating a patient. An authorized user may use the unique identifier associated with the query thyroid image 102 as a reference key to obtain patient data associated the query thyroid image 102 from the secure database.

Even though FIGS. 1 and 2 describe example embodiments of the non-invasive diagnostic system 100 in which the query thyroid image 102 is processed at a single location, e.g., at the computing device (104, 304), one of skill in the art can understand and appreciate that the processing of the query thyroid image 102 may be distributed between different locations without departing from a broader scope of the present disclosure. For example, as illustrated in FIG. 3, a portion of the processing of the query thyroid image 102 may be performed external to the computing device 104 at an analysis server 204, for example.

Figure 3:
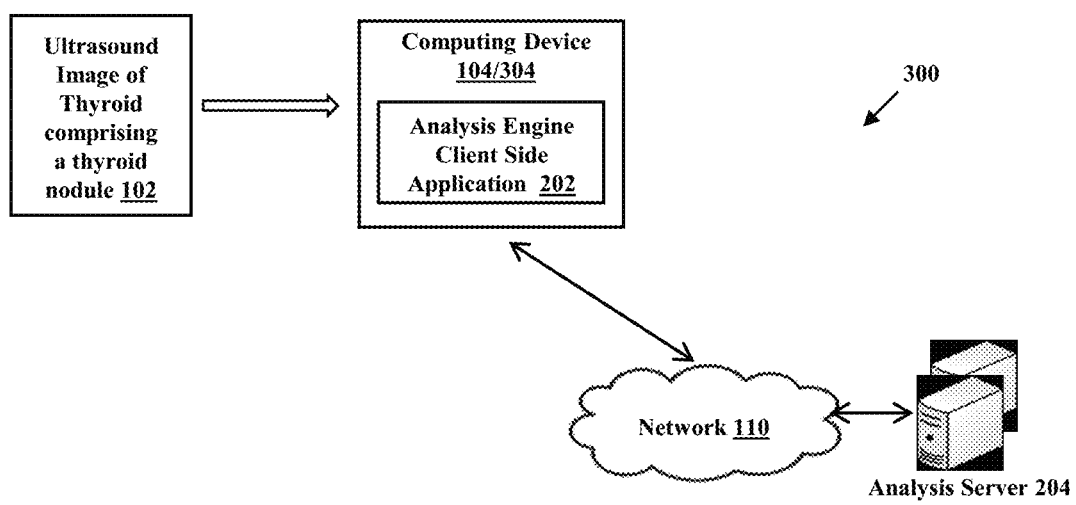
FIG. 3 illustrates yet another example operating environment of the thyroid nodule diagnosis system, in accordance with example embodiments of the present disclosure.

Referring to FIG. 3, this figure illustrates yet another example operating environment of the non-invasive diagnostic system, in accordance with example embodiments of the present disclosure. It is noted that FIG. 3 is substantially similar to FIGS. 1 and 2, except that in the system 300 illustrated in FIG. 3 at least a portion of the processing associated with query thyroid image 102 may be performed in an analysis server 204 that is external to and communicably coupled to the computing device (104, 304) via a wired and/or a wireless network 210. In the example embodiment illustrated in FIG. 3, a client side application 202 of the server 204 may be downloaded and/or installed on the computing device (104, 304). The client side application 202 on the computing device (104, 304) may transmit the query thyroid image 102 to the analysis server 204 (herein 'server 204') via the wired and/or wireless network 210.

In certain example embodiments, the query thyroid image 102 may be transmitted to the server 204 without any processing being done at the computing device (104, 304). Alternatively, in other example embodiments, the client side application 202 may be configured to perform some pre-processing operations on the query thyroid image 102 before transmitting it to the server 204. For example, prior to transmittal to the server 204, the client side application 202 may segment the query thyroid image 102 to generate the query thyroid nodule image. In either case, the client side application 202 may be configured to remove patient data from the unprocessed query thyroid image 102 or the query thyroid nodule image and assign a unique identifier to said image prior to transmitting said image to the server 204.

If the unprocessed query thyroid image 102 is transmitted to the server 204, the server 204 may be configured to segment the query thyroid image 102 to generate the query thyroid nodule image. Then, the server 204 may process, using a machine learning model and/or image similarity technology, the query thyroid nodule image to determine whether the thyroid nodule of interest is malignant or benign. In particular, the server 204 may be configured to generate feature vectors associated with the query thyroid nodule image and use the feature vectors to identify at least one labelled thyroid image that is similar to the query thyroid nodule image. Responsively, the server 204 may generate an output report (e.g., output report 1202) based on one or more labels associated with the at least one labelled thyroid image that is similar to the query thyroid nodule image. Further, the server 204 may be configured to transmit the output report to the computing device (104, 304) for presentation via a display 510 of the computing device (104, 304). In some example embodiments, the server 204 may be configured to transmit the one or more labels associated with at least one labelled thyroid image to the computing device (104, 304), and the output report may be generated by the client side application 202 at the computing device (104, 304). In some other example embodiments, the server 204 may transmit a message to the computing device (104, 304), where the message informs the user thereof that the query thyroid image 102 has been processed and the output report associated with the thyroid nodule of interest has been prepared. The message may include a web link that the user can select via the user interface 512 of the computing device (104, 304). The web link may provide the user access to the output report stored in the server 204. Along with presenting the output report, the client side application 202 in the computing device (104, 304) may be configured to provide an option to the user to verify the data that is presented in the output report as described above. The result of the verification may or may not be sent as feedback to the server 204 to further train and optimize the machine learning model.

In addition to the one or more labels associated with the at least one labelled thyroid image and/or the output report 1202, the server 204 may be configured to transmit the unique identifier associated with the query thyroid image 102 or the query thyroid nodule image back to the computing device (104, 304). For authorized users, the client side application 202 may use the unique identifier to retrieve patient data and present the patient data along with the output report. In some example embodiments, the patient data may only be presented to an authorized user or upon request from an authorized user. In other words, in the example embodiment illustrated in FIG. 3, the query thyroid image 102 or the query thyroid nodule image may be handled at the server 204 solely using the unique identifier, thereby protecting patient data from being transmitted external to a facility such as a hospital in which the computing device (104, 304) may be located.

Figure 4:
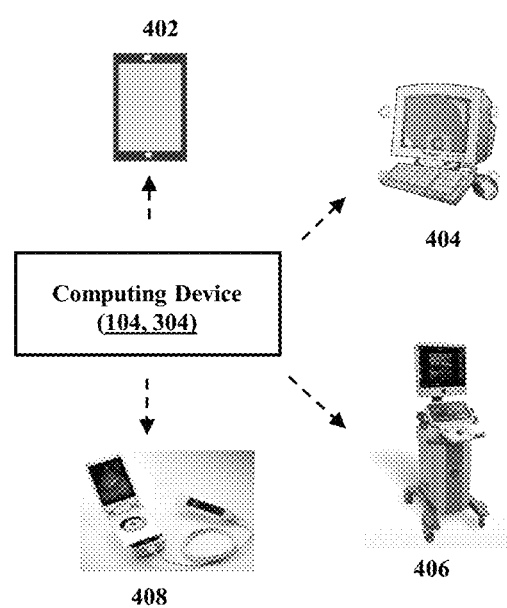
FIG. 4 illustrates example computing devices of the thyroid nodule diagnosis system, in accordance with example embodiments of the present disclosure.

As illustrated in FIG. 4, the computing device, e.g., computing device 104 may include any appropriate stationary computing device such as a desktop 404, mainframe computer, etc., or a portable/hand held computing device 402, such as, but not limited to, a cell phone, a smartphone, a personal digital assistant, a tablet, a phablet, etc. In certain example embodiments, the computing device, e.g., computing device 304 may include a mobile phone 408 with an ultrasound probe that is removably coupled thereto, an ultrasound imaging machine 406, etc.

Figure 5:
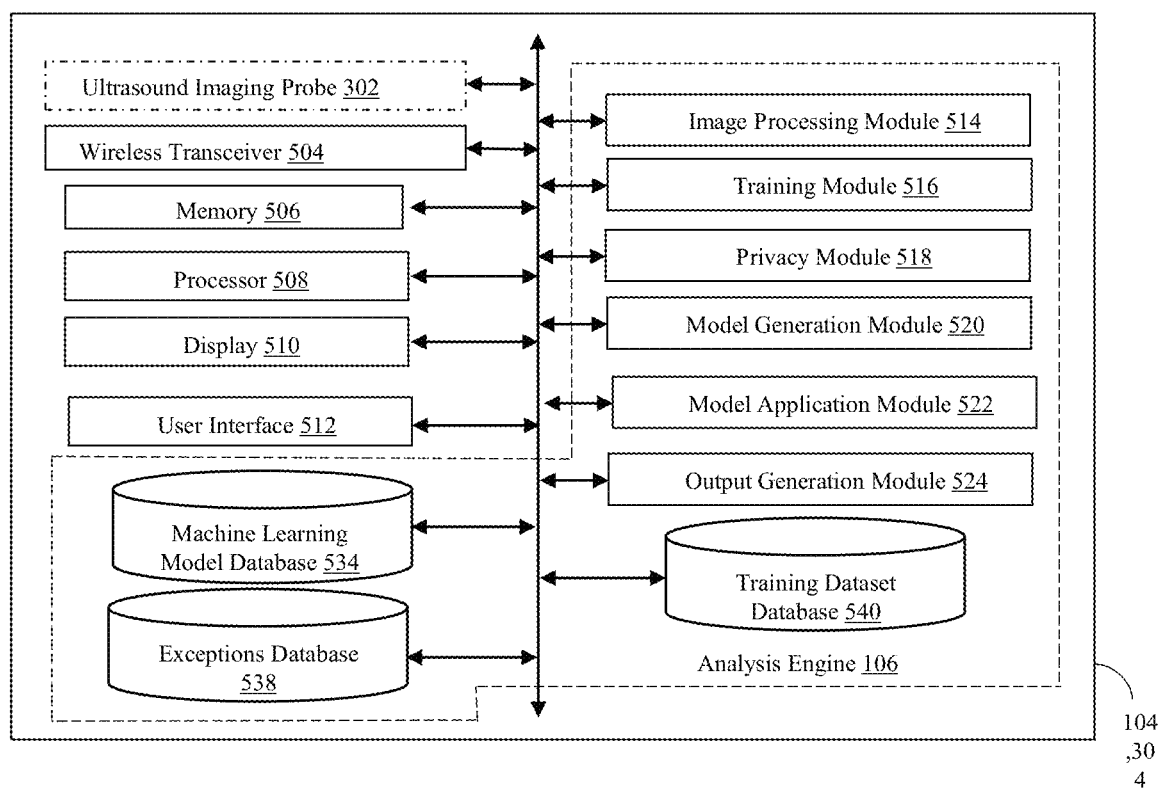
FIG. 5 illustrates a block diagram of the computing device and an analysis server of FIG. 1 and/or FIG. 2, in accordance with example embodiments of the present disclosure.
Figure 6:
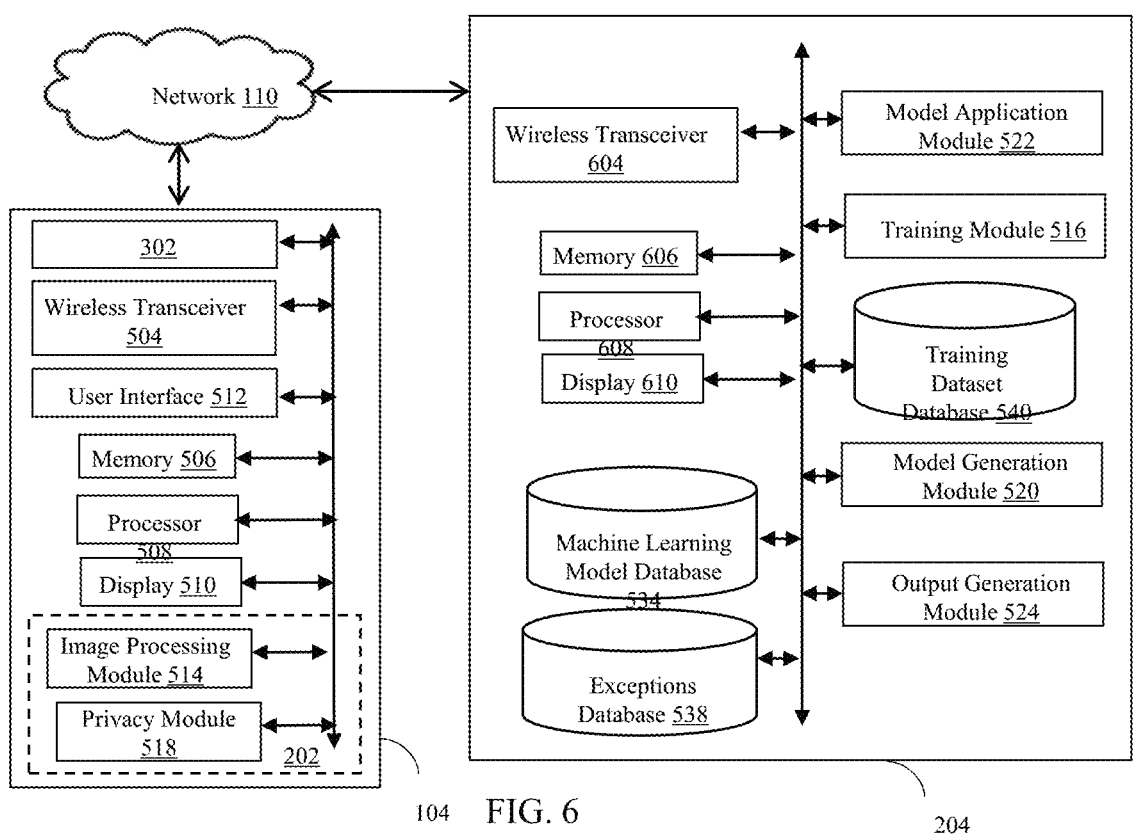
FIG. 6 illustrates a block diagram of the computing device and an analysis server of FIG. 3, in accordance with example embodiments of the present disclosure.

The computing device (104, 304) and the server 204 will be further described below in greater detail in association with FIGS. 5 and 6. Referring to FIG. 5, the computing device (104, 304) may include a wireless transceiver 504, a memory 506, a processor 508, a display 510, a user interface 512, and the analysis engine 106. Optionally, the computing device (e.g., computing device 304) may include an ultrasound imaging probe 502. Even though FIG. 5 illustrates the analysis engine 106 as being disposed in the computing device (104, 304), one of ordinary skill in the art can understand and appreciate that in other example embodiments, as illustrated in FIGS. 3 and 6, the analysis engine 106 may be implemented as a client-server model with the client side application 202 being disposed in the computing device (104, 304) and a server 204 that is disposed external to and communicatively coupled to the computing device (104, 304). In particular, as illustrated in FIG. 6, the computing device (104, 304) may include the optional ultrasound imaging probe 502, a wireless transceiver 504, a memory 506, a processor 508, a display 510, a user interface 512, and the client side application 202. Further, the server 204 may include a processor 608, a wireless transceiver 604, a memory 606, a display 610, and various modules 516 and 520-524 and databases 534, 538, and 540 that are associated with the non-invasive diagnosis of a thyroid nodule of interest.

The processor 508 of the computing device (104, 304) may be a multi-core processor or a combination of multiple single core processors. Further, the computing device (104, 304) may include a memory 506 that is coupled to the processor 508. The memory 506 may be non-transitory storage medium, in one embodiment, and a transitory storage medium in another embodiment. The memory 506 may include instructions that may be executed by the processor 508 to perform operations of the computing device (104, 304), e.g., generating machine learning models, capturing and/or receiving the query thyroid image 102, determining whether the thyroid nodule of interest in the query thyroid image 102 is benign or malignant, etc. In other words, operations associated with the different modules 514-524 of the analysis engine 106, the optional ultrasound imaging probe 502, the wireless transceiver 504, the display 510, and the user interface 512 of the computing device (104, 304) may be executed using the processor 508.

The wireless transceiver 504 of the computing device (104, 304) may be configured to enable communication (wired and/or wireless) to and from the computing device (104, 304). Further, as described above, the user interface 512 may be configured to receive a user input from a user 310 through a visual interaction, an auditory interaction, and/or a tactile interaction. Accordingly, the user interface 512 may include, but is not limited to, a touchscreen, a keypad, a microphone, a gesture recognition device, etc. In certain example embodiments, the display 510 of the computing device (104, 304) may operate as a user interface 512. For example, the display 510 may be a touchscreen display that the user 108 can interact with to capture an ultrasound image that is projected to the display by the optional ultrasound imaging probe 502, to zoom in/zoom out a captured image, and/or for other interactive operations. The display 510 of the computing device (104, 304) may also be configured to visually present: an image as seen by the optional ultrasound imaging probe 502 (image feed), the example output report 1202, etc.

The processor 608, the wireless transceiver 604, the memory 606, and display 610 of the server 204 may be substantially similar to that of the processor 508, the wireless transceiver 504, the memory 506, and display 510 of the computing device (104, 304), except that the processor 608, the wireless transceiver 604, the memory 606, and display 610 of the server 204 may be configured to execute operations associated with the server 204. The processor 608, the wireless transceiver 604, the memory 606, and display 610 of the server 204 may not be described in greater detail for the sake of brevity.

The operation of the various modules 512-524 and databases 534, 538, and 540 embodied in the analysis engine 106, the client side application 202, and/or the server 204 will be described below in greater detail in association with FIGS. 7-11 by referring to FIGS. 5-6 and 12 which illustrates the various example components of the computing device (104, 304), the analysis engine 106 disposed in the computing device (104, 304), the client side application 202, and server 204. FIGS. 7-8, 10, and 11 illustrate flowcharts associated with the operation of the analysis engine 106; and FIG. 9 illustrates a flowchart associated with the operation of the client side application 202 and the server 204. Although specific operations are disclosed in the flowcharts illustrated in FIGS. 7-11, such operations are only non-limiting examples. That is, embodiments of the present invention are well suited to performing various other operations or variations of the operations recited in the flowcharts. It is appreciated that the operations in the flowcharts illustrated in FIGS. 7-11 may be performed in an order different than presented, and that not all the operations in the flowcharts may be performed.

All, or a portion of, the embodiments described by the flowcharts illustrated in FIGS. 7-11 can be implemented using computer-readable and computer-executable instructions which reside, for example, in a memory of the computing device (104, 304) and/or the server 204. As described above, certain processes and operations of the present invention are realized, in one embodiment, as a series of instructions (e.g., software programs) that reside within computer readable memory of a computer system and are executed by the processor of the computer system. When executed, the instructions cause the computer system to implement the functionality of the present invention as described below.

Figure 7:
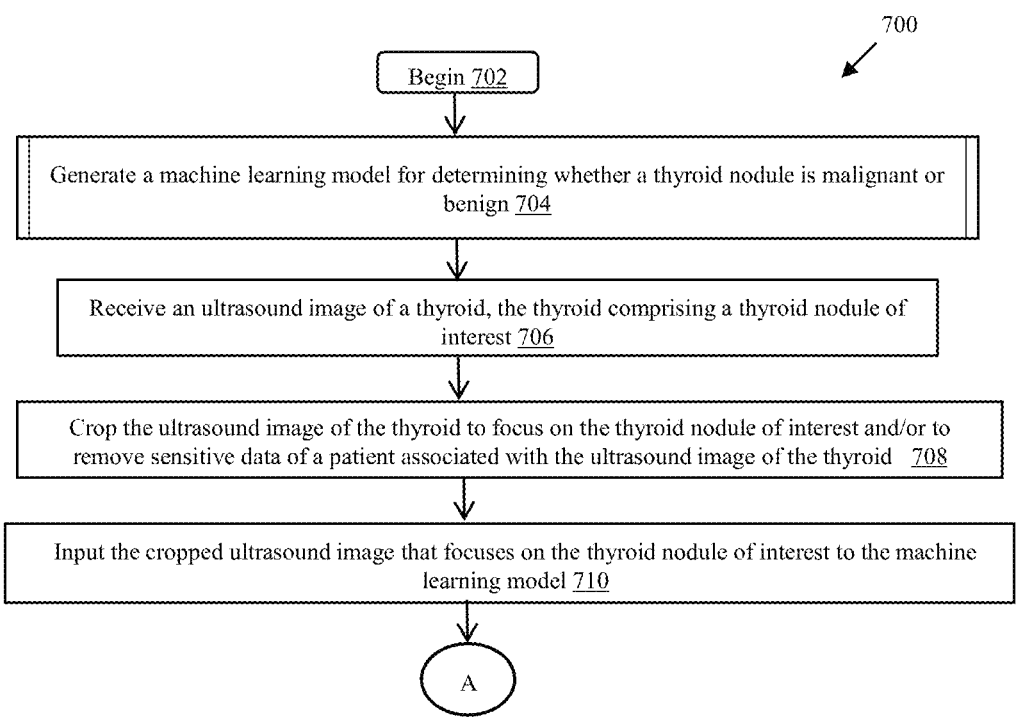
FIGS. 7-8 illustrate an example operation of the analysis engine of the thyroid nodule diagnosis system illustrated in FIG. 1 and FIG. 2, in accordance with example embodiments of the present disclosure.
Figure 8:
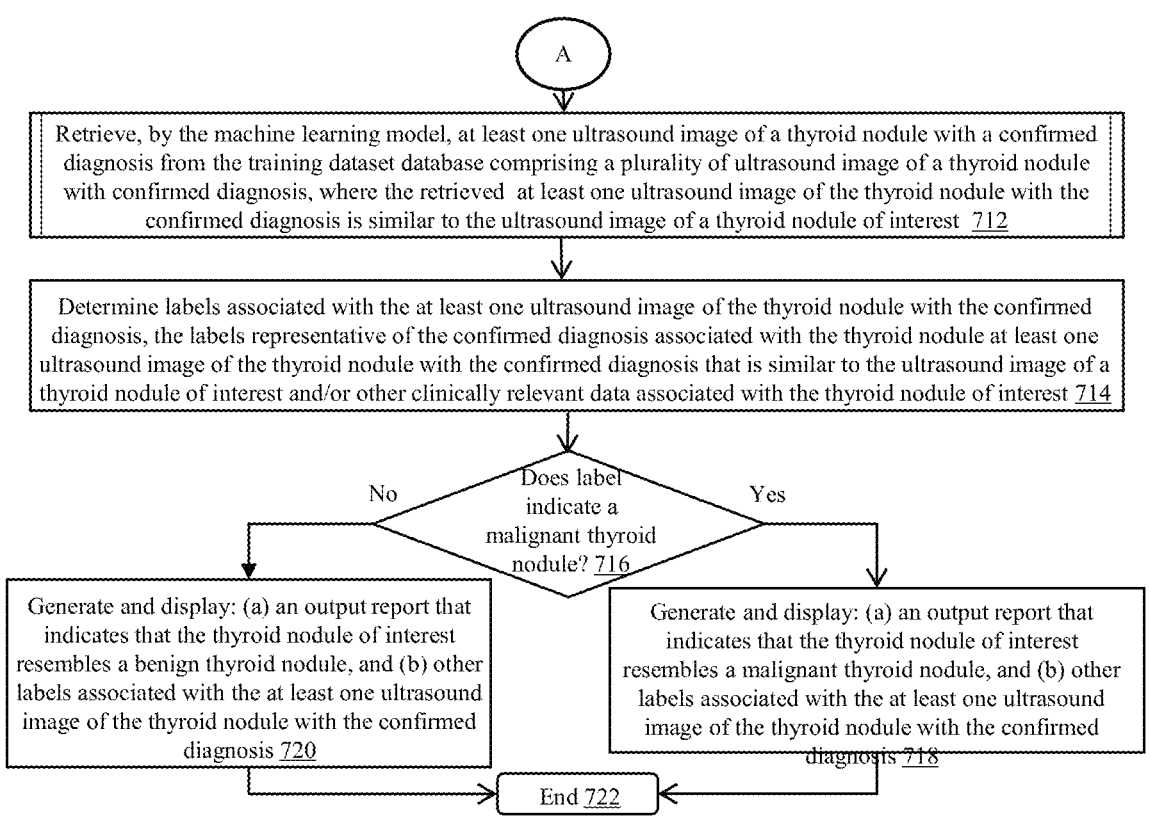
Figure 9:
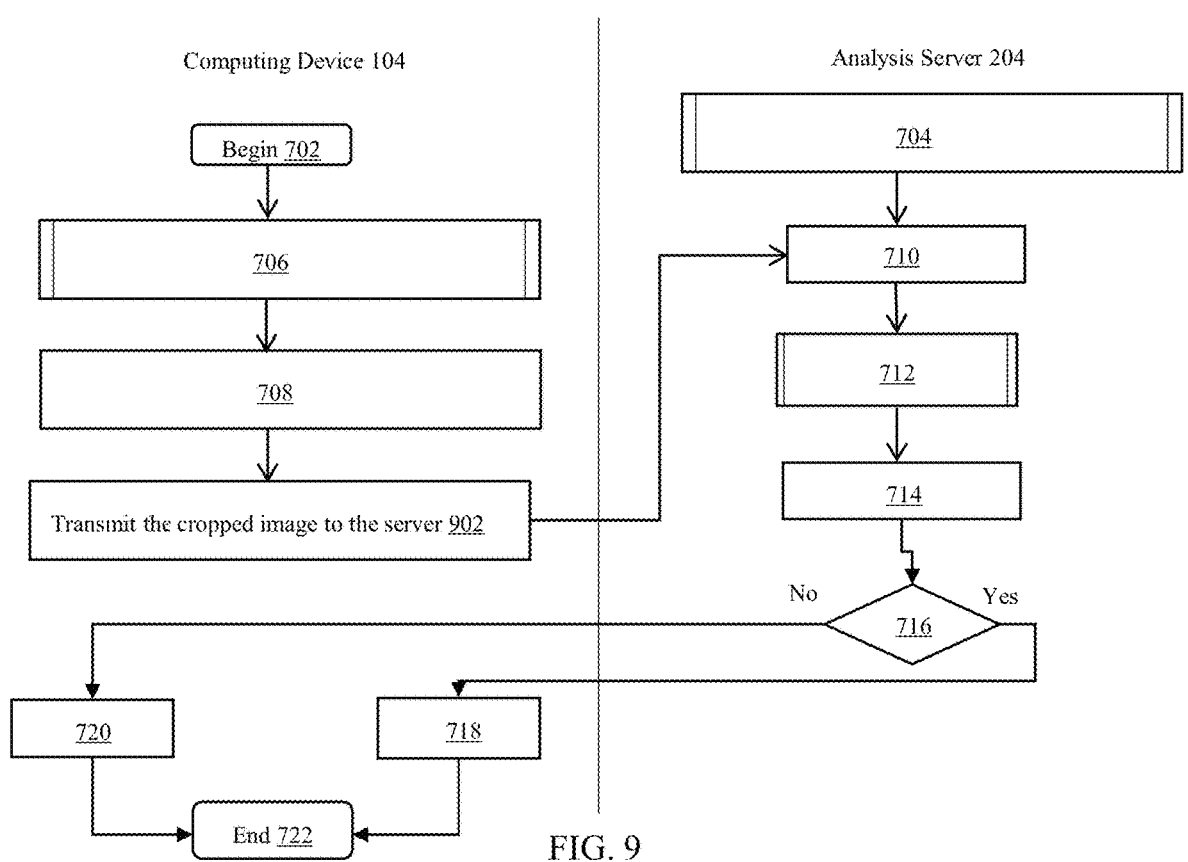
FIG. 9 illustrates another example operation of the analysis engine of the thyroid nodule diagnosis system illustrated in FIG. 3, in accordance with example embodiments of the present disclosure.

Turning to FIGS. 7-8, these figures illustrate an example thyroid nodule diagnosis process 700 of the analysis engine 106 illustrated in FIGS. 1 and 2, in accordance with example embodiments of the present disclosure. The thyroid nodule diagnosis process 700 begins at operation 702 and proceeds to operation 704 where a training module 516 of the computing device (104, 304) may operate in concert with the model generation engine 520 to train an image similarity machine learning algorithm and generate an image similarity machine learning model. Operation 704 associated with generating the machine learning model will be described in greater detail below, in association with FIG. 10.

Figure 10:
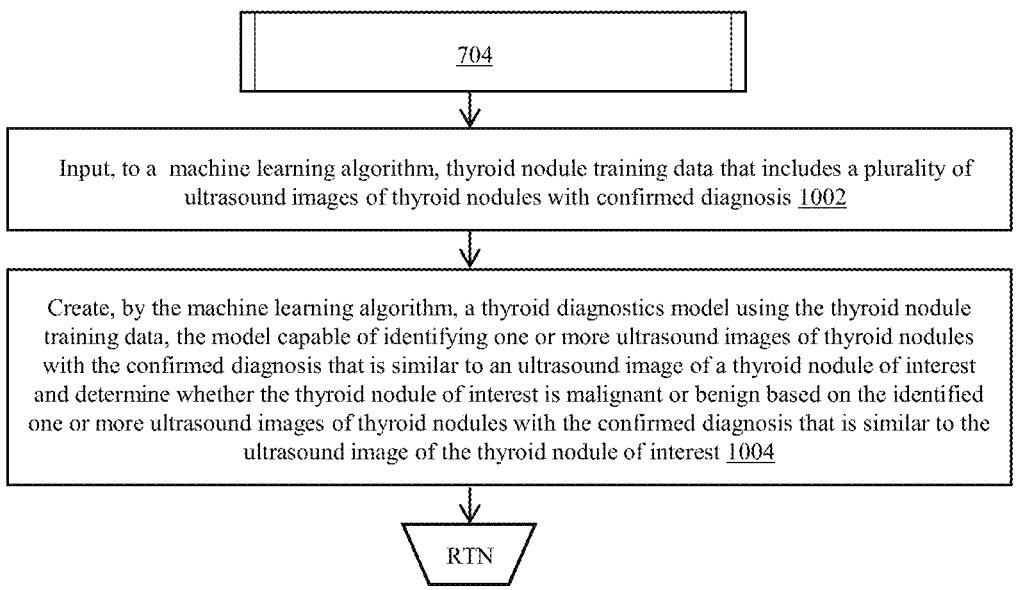
FIG. 10 illustrates an example machine learning model generation operation of the thyroid nodule diagnosis system, in accordance with example embodiments of the present disclosure.

Referring to FIG. 10, an example machine learning model generation process 1000 of the analysis engine 106 may begin at operation 1002. In operation 1002, the training module 516 may input a plurality of labelled thyroid images from a training dataset database 540 to an image similarity machine learning algorithm in the training module 516. As described above, an example image similarity machine learning algorithm of the present disclosure may include an image classification multi-layer neural network algorithm such as an image classification convolutional neural network algorithm that has been modified for image similarity analysis by removing one or more layers (e.g., the final fully connected layer(s), the final output layer, etc.) of the image classification multi-layer neural network algorithm that are used for classifying an image into various categories. Said image similarity machine learning algorithm of the present disclosure may be configured to perform convolution, pooling, and/or flattening operations on a given image to generate a feature vector associated with the given image, but the image similarity machine learning algorithm may not be configured to perform operations associated with the fully connected layers that classify the image into one or more categories. Instead, the machine learning algorithm may be configured to use the feature vector of the given image to identity one or more other images that are similar to the given image using image similarity determination techniques.

The training dataset database 540 may be created by collecting numerous labelled thyroid images from any appropriate data source, such as an ultrasound machine, from a pre-existing medical image database or server, etc. For example, the training dataset database 540 may include thousands or millions of labelled thyroid images. In some example embodiments, the labelled thyroid images may be sourced directly by physicians, lab technicians, radiologists, etc. That is, the training dataset database 540 may partly be created by crowdsourcing where different users such as, but not limited to, physicians, lab technicians, radiologists, patients, medical professionals etc., may upload the labelled thyroid images to the training dataset database 540. It is understood that the uploaded labelled thyroid images may be devoid of patient data to comply with the medical privacy laws (e.g., HIPAA laws).

Each labelled thyroid image of the training dataset database 540 may include an ultrasound image of a thyroid nodules that have a confirmed diagnosis associated therewith. Each ultrasound image in the training dataset database 540 (e.g., labelled thyroid image) may be labelled using one or more labels that represent the confirmed diagnosis data associated with the thyroid nodule in the ultrasound image. The confirmed diagnosis data of the nodules may include, but is not limited to, benign thyroid nodule, malignant thyroid nodule, papillary thyroid cancer, follicular variant of papillary thyroid cancer, follicular cancer, hurthle cell cancer, anaplastic thyroid cancer, medullary thyroid cancer, follicular adenoma, thyroid lymphoma, colloid nodule, spongiform nodule, thyroid cyst, thyroiditis, pseudo nodule, genetic mutations, etc. The confirmed diagnosis data may also include other characteristics associated with the nodule such as, but not limited to, taller than wider, irregular margins, halo, colloid streaks, colloid comet tail, micro calcifications, macro calcifications, cyst, cystic degeneration, extrathyroidal extension, hypoechoic, hyperechoic, isoechoic etc.

In other words, the training dataset database 540 may include ultrasound images of both benign and malignant thyroid nodules that have been labelled with data (medically relevant diagnosis data, imaging characteristic data, genetic mutation data, etc.) associated with the nodules. In some examples, the ultrasound images (e.g., labelled thyroid images) in the training dataset database 540 may also be labelled with other clinically useful labels such as risk of recurrence, probable prognosis, probable treatment options, etc.

Returning to FIG. 10, responsive to receiving the labelled thyroid images from the training dataset database 540, in operation 1004, the machine learning algorithm of the training module 516 may operate in concert with the model generation module 520 to create a machine learning model, e.g., an image similarity machine learning model that is trained using the plurality of labelled thyroid images. That is, the machine learning model may be generated as an initial set-up, i.e., prior to capturing or receiving the query thyroid image 102. In particular, once the plurality of labelled thyroid images are provided, the image similarity machine learning algorithm of the training module 516 may operate in concert with the model generation module 520 to find patterns in the plurality of labelled thyroid images that map the input data attributes of the plurality of labelled thyroid images to a target such as the one or more labels associated with the plurality of labelled thyroid images. Responsive to finding or learning the pattern, the model generation module 520 creates a machine learning model that captures said patterns. The machine learning model is then used by the analysis engine 106 to get predictions on new data, e.g., a query thyroid image that needs to be diagnosed (i.e., no diagnosis information is available). Different training methods such as supervised training, semi-supervised training, etc., may be used to train the machine learning model.

In one example, the machine learning model may be configured to: (a) generate feature vectors associated with a given image such as the query thyroid image 102, (b) use the feature vectors to identify one or more labelled thyroid images in the training dataset database 540 that are similar to the query thyroid image 102, and (c) output the labels associated with the one or more labelled thyroid images in the training dataset database 540 that are identified as being similar to the query thyroid image 102. That is, when a query thyroid image 102 is provided as input, the machine learning model may be configured to output one or more labels associated with labelled thyroid image(s) in the training dataset database 540 that are similar to the query thyroid image 102. In some example embodiments, in addition to or instead of outputting the labels associated with the labelled thyroid image(s) in the training dataset database 540 that are similar to the query thyroid image 102, the machine learning model may be configured to output the labelled thyroid image(s) that are similar to the query thyroid image 102 for an operator to view. The display of the labelled thyroid image(s) that are similar to the query thyroid image 102 may help a physician to validate the analysis of the machine learning model.

Alternatively, in some examples, the machine learning model may only be configured to generate feature vectors associated with a given image such as the query thyroid image 102. That is, in said examples, the machine learning model may not be configured to identify one or more labelled thyroid images in the training dataset database 540 that are similar to the query thyroid image 102 and output the labels associated with the one or more labelled thyroid images. Accordingly, in said examples, when a query thyroid image 102 is provided as input, the machine learning model may be configured to output feature vectors associated with the query thyroid image 102. In said examples, the machine learning model may operate in concert with an image similarity algorithm of the output generation module 524 to use the feature vectors of the query thyroid image 102 to identify one or more labelled thyroid images in the training dataset database 540 that are similar to the query thyroid image 102, and/or output the labels associated with the one or more labelled thyroid images in the training dataset database 540 that are identified as being similar to the query thyroid image 102.

In some example embodiment, the training and generation of the machine learning model may be completed outside of the computing device (104/304) and/or server 204 and only the pre-trained machine learning model may be stored in the computing device (104/304) and/or server 204.

Further, in operation 1004, responsive to creating the machine learning model, the model generation module 520 may store the machine learning model in the machine learning model database 534. Additionally, in operation 1004, once the machine learning model is created, the training module 516 and/or the output generation module 524 may operate in concert to generate feature vectors associated with each labelled thyroid image of the training dataset database 540 using the machine learning model. The feature vectors associated with each labelled thyroid image of the training dataset database 540 may be stored in the machine learning model database 534.

In one or more example embodiments, the training dataset database 540 may be updated periodically to add labelled thyroid images. The data from the updated training dataset database 540 may then be used by the image similarity machine learning algorithm to update and train the machine learning model to account for the newer labelled thyroid images. Further, even though FIG. 5 illustrates the training dataset database 540 as being configured in the computing device (104/304) and FIG. 6 illustrates the training dataset database 540 as being configured in the server 204, one of ordinary skill in the art can understand and appreciate that in other example embodiments, the training dataset database 540 may be disposed external to the computing device (104/304) and/or the server 204. For example, the training dataset database 540 may be a cloud hosted database. Further, the machine learning model described above is non-limiting. That is, other appropriate machine learning models configured to perform other operations associated with the non-invasive thyroid nodule diagnosis are not outside the broader scope of the present disclosure.

Once the machine learning model is generated, the example machine learning model generation process 1000 returns to operation 706 of FIG. 7. Returning to FIG. 7, in operation 706, a query thyroid image 102 may be sent to the image processing module 514. As described above in association with FIGS. 1-3, the computing device (104, 304) may receive the query thyroid image 102 from an external source through wireless and/or wired communication link. Alternatively, the computing device 304 may capture the query thyroid image 102 using the ultrasound imaging probe 302. In one example embodiment, the received or captured query thyroid image 102 may be forwarded to the image processing module 514. However, in other example embodiments, the received or captured query thyroid image 102 may be stored in a memory 506 of the computing device (104, 304) and retrieved by the image processing module 514. Prior to storing the query thyroid image 102 in the memory 506 or forwarding the query thyroid image 102 to the image processing module 514, the processor 508 of the computing device (104, 304) may operate in concert with the privacy module 518 to determine if patient data has been removed from the query thyroid image 102. If the patient data has not been removed, the privacy module 518 may be configured to remove the patient data from the query thyroid image 102, store said patient data in a secure database, and assign a unique identifier to the query thyroid image 102. As described above, only authorized users may be provided access to the patient data stored in the secure database. Users may be authorized using any appropriate authorization mechanisms, such as username and password combinations, fingerprints, retina scans, facial recognition, voice prints, etc. In some example embodiments, the patient data that is stored in the secure database may be configured to be deleted after the output report 1202 associated with query thyroid image 102 is generated and presented or after the patient data has been stored in the secure database for a predetermined time period (e.g., if the computing device 104 on which the patient data is stored is a personal computing device of a medical professional such as the medical professional's smartphone.).

Even though the present disclosure describes a privacy measure where the patient data is removed from the query thyroid image 102 and stored in a secure database prior to processing the query thyroid image 102 for later access by authorized users, one of skill in the art can understand and appreciate that in other example embodiments, the privacy module 518 of the analysis engine 106 may use any other appropriate privacy measures or techniques to comply with the data privacy laws in the medical field (e.g., HIPAA laws).

Responsive to receiving the query thyroid image 102 from which the patient data has been removed, in operation 708, the image processing module 514 may be configured to segment or crop the query thyroid image 102 to generate a query thyroid nodule image. As described above, the query thyroid image 102 may be an ultrasound image of a thyroid comprising a thyroid nodule of interest, and the query thyroid nodule image may be an ultrasound image of said thyroid nodule of interest.

In one example embodiment, in operation 708, the image processing module 514 may communicate with the user interface 512 and the display 510 to generate a query requesting the user to input the location of the thyroid nodule of interest in the query thyroid image 102. For example, the query may present the query thyroid image 102 and request the user to identify the location of the thyroid nodule or a portion of the display screen 510 that corresponds to the location of the thyroid nodule of interest within the presented query thyroid image, i.e., the ultrasound image of the thyroid comprising the thyroid nodule of interest. In another example embodiment, the image processing module 514 of the analysis engine 106 may be configured to automatically determine a location of the thyroid nodule of interest in the query thyroid image 102 using a machine learning. For example, in operation 704, in addition to creating an image similarity machine learning model, the model generation module 520 may be configured to create a location determination machine learning model by training the machine learning algorithm using the same labelled thyroid images in the training dataset database 540, where the location determination machine learning model may be configured to look for certain features associated with thyroid nodule in an ultrasound image of a thyroid to automatically determine the location of the thyroid nodule. In said other example embodiment, the query thyroid image 102 may be fed to said location determination machine learning model to automatically determine the location of the thyroid nodule of interest.

Once the location of the thyroid nodule of interest in the query thyroid image 102 is determined, in operation 708, the image processing module 514 may segment or crop a portion of the query thyroid image corresponding to the thyroid nodule of interest to obtain the query thyroid nodule image that focuses on the thyroid nodule of interest. In some example embodiments, a query thyroid image may include more than one thyroid nodule. In said example embodiments, the query thyroid image may be segmented or cropped to generate multiple query thyroid nodule images, where each query thyroid nodule image is associated with an individual thyroid nodule of the more than one thyroid nodules.

After generating the query thyroid nodule image, in operation 710, the image processing module 514 may be configured to forward the query thyroid nodule image to the model application module 522. However, prior to forwarding the query thyroid nodule image to the model application module 522, in operation 710, the image processing module 514 may be configured to make various adjustments to the image characteristics of the query thyroid nodule image as needed. For example, the image processing module 514 may enhance a brightness, contrast, color, etc., of the query thyroid nodule image. Further, the image processing module 514 may be configured to flip the colors of the image. That is, if nodule is in black and the background is white, the image processing module 514 may flip the colors such that the nodule appears in white and the background in black to better define the borders and/or other features of the nodule. It is noted that in addition to the above described adjustments to the image characteristics of the query thyroid nodule image, any other appropriate image enhancement adjustments are within the broader scope of the present disclosure.

Upon receiving the query thyroid nodule image, in operation 710, the model application module 522 may input the query thyroid nodule image to the machine learning model (i.e., the image similarity machine learning model). Then, in operation 712, the query thyroid nodule image may be processed using the machine learning model (i.e., the image similarity machine learning model) to determine whether the thyroid nodule of interest in the query thyroid nodule image is benign or malignant along with other relevant data associated with the thyroid nodule. Operation 712 may be described in further detail in association with FIG. 11.

Figure 11:
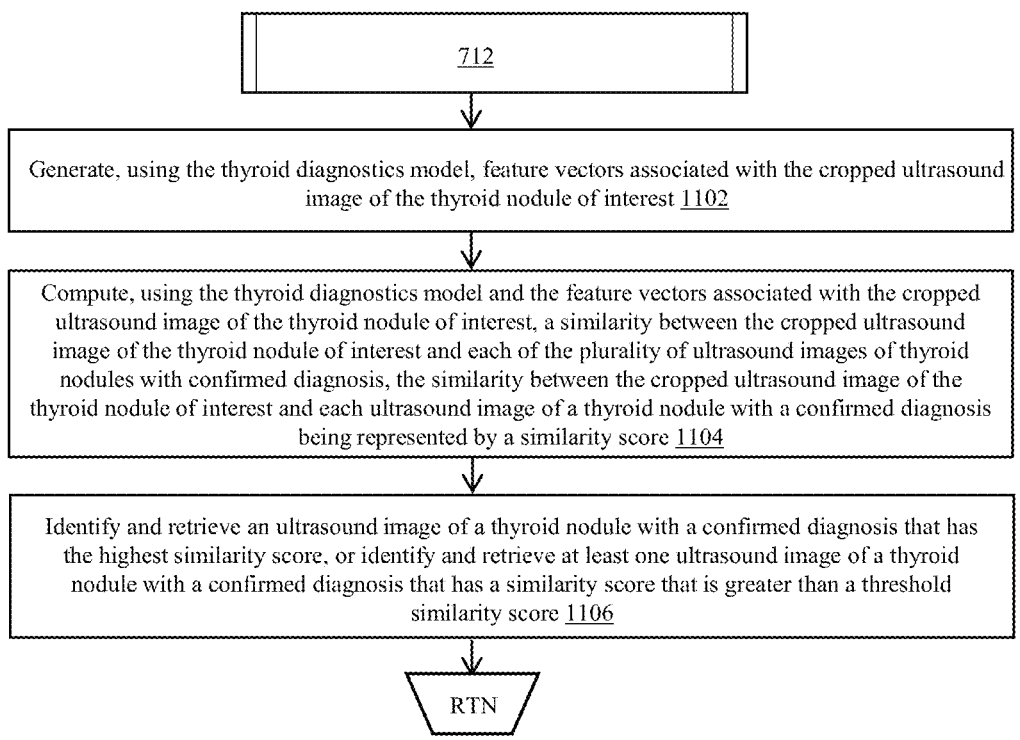
FIG. 11 illustrates an example operation of the example machine learning model of the thyroid nodule diagnosis system, in accordance with example embodiments of the present disclosure.

Referring to FIG. 11, the operation of the machine learning model proceeds begins at operation 1102 where the machine learning model may generate a feature vector associated with the query thyroid nodule image. In one example, the machine learning model may apply pixel level processing on the query thyroid nodule image using convolution filter operations and sub-pooling operations to generate multiple pooled feature maps that represent various high-level and/or low-level features of the thyroid nodule of interest in the query thyroid nodule image such as, but not limited to edges, colors, textures, bodies, etc. In said example, the machine learning model may flatten the multiple pooled feature maps to generate the single feature vector that may be represented using a matrix such as 1*N or N*1 matrix, for example.

Responsive to generating the feature vector associated with the query thyroid nodule image, in operation 1104, the machine learning model may determine N-nearest neighbors of the query thyroid nodule image from the plurality of labelled thyroid images in the training dataset database 540 using the feature vectors of the query thyroid nodule image and the plurality of labelled thyroid images. The N-nearest neighbors may represent N number of labelled thyroid images from the plurality of labelled thyroid images in the training dataset database 540 that are most similar to the query thyroid nodule image.

In particular, to determine the N-nearest neighbors of the query thyroid nodule image, in operation 1104, the machine learning model may compute a similarity between the query thyroid nodule image and each of the plurality of labelled thyroid images in the training dataset database 540 using inner-product methods such as cosine similarity or euclidean distance where inner-product of the feature vectors of the query thyroid nodule image and each of the plurality of labelled thyroid images are calculated. The inner-product values between the query thyroid nodule image and each of the plurality of labelled thyroid images may be stored in the machine learning model database 534 as similarity scores that represent the similarity between the query thyroid nodule image and each of the plurality of labelled thyroid images. Then, in operation 1106, the machine learning model may either select or identify a labelled thyroid image having the highest similarity score with respect to the query thyroid nodule image or select the labelled thyroid images with the top-N similarity scores (e.g., top 10 similarity scores). Alternatively, in operation 1106, the machine learning model may select or identify labelled thyroid images that have a similarity score that is above a threshold similarity score. In either case, responsive to identifying and/or selecting the labelled thyroid image(s) that are similar to the query thyroid nodule image (hereinafter 'selected labelled thyroid images'), the operation of the machine learning model returns to operation 714 of FIG. 8.

In some example embodiments, in operation 1106, the model application module 522 may be configured to transmit the selected labelled thyroid image(s) and/or the labels associated with the selected labelled thyroid image(s) to the output generation module 524. In the example embodiment where the machine learning model is configured to select labelled thyroid images that have a similarity score above a threshold similarity score, if there are no labelled thyroid images that have a similarity score that is above the threshold similarity score, the machine learning model may revert to selecting the labelled thyroid image having the highest similarity score or the labelled thyroid images with the top-N similarity scores. Alternatively, in some example embodiments, if there are no labelled thyroid images that have a similarity score that is above the threshold similarity score, the machine learning model may return an error message or a message indicating no similar labelled images to the output generation module 524.

In some example embodiments, the image similarity machine learning model may only be configured to generate the feature vector associated with the query thyroid nodule image. In said some example embodiments, the operation of the machine learning model may not include operations 1104 and 1106, and the feature vector of the query thyroid nodule image may be returned to the output generation engine 524 which in turn computes the similarity score and identifies the nearest neighbors of the query thyroid nodule image. In other example embodiments where image similarity machine learning model may only be configured to generate the feature vector associated with the query thyroid nodule image, the machine learning model may be configured to transmit the feature vector of the query thyroid nodule image to another machine learning model that is configured to determine the nearest neighbors of the query thyroid nodule image. That is, in said other example embodiments, operations 1104 and 1106 may be performed by another machine learning model that is configured to determined nearest neighbors.

Returning to FIG. 8, in operation 714, the output generation module 524 may be configured to determine or retrieve the labels associated with the selected labelled thyroid images. However, if the output generation module 524 receives the labels associated with the selected labelled thyroid image(s) from the machine learning model, then, operation 714 may be omitted. In either case, upon obtaining the labels associated with the selected labelled thyroid images, in operation 716, the output generation engine 524 may be configured to use the labels to determine whether the thyroid nodule of interest in the query thyroid nodule image that is generated from the query thyroid image 102 is malignant or benign. In particular, in operation 716, if the output generation module 524 determines that the selected thyroid nodule images are malignant thyroid nodules based on the labels associated therewith, the thyroid nodule diagnosis process 700 proceeds to operation 718. Alternatively, in operation 716, if the output generation module 524 determines that the selected thyroid nodule images are not malignant nodule, i.e., they are benign thyroid nodules based on the labels associated therewith, the thyroid nodule diagnosis process 700 proceeds to operation 720.

In operation 718, the output generation module 524 generates an output report (e.g., output report 1202) that indicates that the thyroid nodule of interest of the query thyroid image 102 resembles a malignant thyroid nodule or resembles a labelled thyroid image in the training dataset database 540 that is a malignant thyroid nodule. Similarly, in operation 720, the output generation module 524 generates an output report (e.g., output report 1202) that indicates that the thyroid nodule of interest of the query thyroid image 102 resembles a benign thyroid nodule or resembles a labelled thyroid image in the training dataset database 540 that is a benign thyroid nodule.

In addition to indicating whether the thyroid nodule of interest in the query thyroid image 102 resembles a malignant or benign thyroid nodule, the output generation module 524 may be configured to optionally include other additional data associated with the thyroid nodule of interest in the output report 1202 based on a requirement of the user (e.g., user 310). For example, the output report 1202 may include the query thyroid image 102 or the query thyroid nodule image, the patient data associated with the query thyroid image 102, the labelled thyroid image(s) that are similar to the query thyroid nodule image (i.e., or images of similar thyroid nodules as determined by the machine learning model), and/or clinically useful information such as imaging characteristics of the thyroid nodule, risk of recurrence, probable prognosis, probable treatment options, probable associated mutations or genetic variations based on the labels and/or available medical data.

Further, in operations 718 and 720, the output generation module 524 may be configured to present the output report 1202 via the display 510 of the computing device (104, 304). In some example embodiments, all of the data associated with the thyroid nodule of interest may be displayed in the output report. However, in other example embodiments, the output report 1202 may initially only include information that indicates whether the thyroid nodule of interest resembles a malignant or benign thyroid nodule. In said other example embodiments, the output report 1202 may include drill down features (clickable electronic links, drop down menu, clickable tabs, etc.) that the user can interact with to drill down and see or obtain the additional clinically relevant information, patient data, etc. Prior to providing the patient data, the analysis engine 106 may require the user 310 to be authenticated. However, in other example embodiments, in addition to presenting the output report 1202, in operations 718 and 720, analysis engine 106 of the computing device (104, 304) may generate and present a message via the display 510, where the message requests the user 310 to verify the accuracy of the data in the output report 1202. Responsive to a positive verification result, the query thyroid image 102 may be stored in the training dataset database 540 as a labelled thyroid image for providing further feedback to and optimizing the machine learning model. However, responsive to a negative verification result, the query thyroid image 102 may be identified as and stored in an exceptions database 538 as an exception and provided as feedback to further train and optimize the one or more machine learning model. In some example embodiments, the verification process may be omitted without departing from a broader scope of the present disclosure. Further, the thyroid nodule diagnosis process 700 ends in operation 722.

Turning to FIG. 9, this figure illustrates another example thyroid nodule diagnosis process associated with the system illustrated in FIG. 3, in accordance with example embodiments of the present disclosure. It is noted that FIG. 9 is substantially similar to FIGS. 7-8 except that the operations 702, 706, 708, and 718-722 of the thyroid nodule diagnosis process are performed by the client side application 202 at the computing device (104, 304) and the operations 704 and 710-716 are performed at the server 204 that is remote from and communicably coupled to the computing device (104, 304) via a network 110. Operations 702-722 of FIG. 9 have been described above in greater detail in association with FIGS. 7-8 and will not be repeated herein for the sake of brevity. As illustrated in FIG. 9, once the query thyroid nodule image has been generated with the patient data removed therefrom, in operation 902, the computing device (104, 304) may transmit the query thyroid nodule image to the server 204 over the network 110 using the wireless transceiver 504. In some example embodiments, the process of generating the query thyroid nodule image from the query thyroid image 102 may also be performed at the server 204. However, the computing device (104, 304) may remove the patient data from the query thyroid image 102 prior to transmitting the query thyroid image 102 to the server 204. Further, in the example embodiment illustrated in FIG. 9, the server 204 may generate the output report 1202 and transmit the output report 1202 to the computing device (104, 304) for presentation via the display 510 thereof. Alternatively, in some example embodiments, the output generation module 524 may be disposed in the computing device (104, 304) and operations 716-722 or 714-722 may be performed at the computing device (104, 304). In yet another example embodiment, operations 716-722 may be performed at the server 204 and the server 204 may send a message with a weblink to the computing device (104, 304) such that the user 310 may click the weblink to obtain access to the output report 1202 in the server 204.

Although the present embodiments have been described with reference to specific example embodiments, it will be evident that various modifications and changes may be made to these embodiments without departing from the broader spirit and scope of the various embodiments. For example, the various devices and modules described herein may be enabled and operated using hardware circuitry (e.g., CMOS based logic circuitry), firmware, software or any combination of hardware, firmware, and software (e.g., embodied in a machine readable medium). For example, the various electrical structures and methods may be embodied using transistors, logic gates, and electrical circuits (e.g., application specific integrated (ASIC) circuitry and/or in Digital Signal Processor (DSP) circuitry).

The terms "invention," "the invention," "this invention," and "the present invention," as used herein, intend to refer broadly to all disclosed subject matter and teaching, and recitations containing these terms should not be misconstrued as limiting the subject matter taught herein or to limit the meaning or scope of the claims. From the description of the exemplary embodiments, equivalents of the elements shown therein will suggest themselves to those skilled in the art, and ways of constructing other embodiments of the present invention will appear to practitioners of the art. Therefore, the scope of the present invention is to be limited only by the claims that follow.

In addition, it will be appreciated that the various operations, processes, and methods disclosed herein may be embodied in a machine-readable medium and/or a machine accessible medium compatible with a data processing system (e.g., a computer system), and may be performed in any order (e.g., including using means for achieving the various operations). Accordingly, the specification and drawings are to be regarded in an illustrative rather than a restrictive sense.

What is claimed is:

1. A system comprising:
a computing device that comprises:
an ultrasound imaging apparatus that is configured to capture an ultrasound image of a thyroid comprising a thyroid nodule of interest; and
an analysis engine that is configured to:
generate, using a machine learning algorithm and a training dataset, a machine learning model that is configured to determine at least one labelled thyroid image that is similar to an ultrasound image of the thyroid nodule of interest,
wherein the machine learning algorithm comprises a multi-layer neural network algorithm that has been modified by removing a final fully connected classification layer, and
wherein the training dataset comprises a plurality of labelled thyroid images, and wherein each labelled thyroid image comprises an ultrasound image of a thyroid nodule that has a confirmed diagnosis;
receive the ultrasound image of the thyroid captured by the ultrasound imaging apparatus;
segment the ultrasound image of the thyroid to generate the ultrasound image of the thyroid nodule of interest;
process, using the machine learning model, the ultrasound image of the thyroid nodule of interest to determine the at least one labelled thyroid image from the plurality of labelled thyroid images that is similar to the ultrasound image of the thyroid nodule of interest;
determine, based on the at least one labelled thyroid image, whether the thyroid nodule of interest is one of a malignant thyroid nodule and a benign thyroid nodule,
wherein the at least one labelled thyroid image comprises multiple labelled thyroid images that have been determined by the machine learning model to be similar to the ultrasound image of the thyroid nodule of interest; and
generate and display an output report that comprises:
(a) the multiple labelled thyroid images, and
(b) an identification of whether the thyroid nodule of interest resembles one of the malignant thyroid nodule and the benign thyroid nodule based on a labelled thyroid image of the multiple labelled thyroid images.

2. The system of claim 1, wherein to determine the at least one labelled thyroid image that is similar to the ultrasound image of the thyroid nodule of interest, the analysis engine is configured to:

generate, using the machine learning model, a first feature vector associated with the ultrasound image of the thyroid nodule of interest; and
for each of the plurality of labelled thyroid images, compute a similarity score that represents a similarity between the ultrasound image of the thyroid nodule of interest and the respective labelled thyroid image based on the first feature vector associated with the ultrasound image of the thyroid nodule of interest and a second feature vector associated with the respective labelled thyroid image, and
identify the at least one labelled thyroid image that has a similarity score that is above a threshold similarity score.

3. The system of claim 1:
wherein the multiple labelled thyroid images are arranged in an order of a similarity of each of the multiple labelled thyroid image with the ultrasound image of the thyroid nodule of interest, the similarity being computed based on a feature vector associated with the ultrasound image of the thyroid nodule of interest.

4. The system of claim 2, wherein the similarity score is computed using cosine similarity.

5. The system of claim 1, wherein the similarity score is computed using Euclidean distance.

6. The system of claim 1:
wherein to determine whether the thyroid nodule of interest is one of the malignant thyroid nodule and the benign thyroid nodule, the analysis engine is configured to:
determine, using labels associated with the labelled thyroid image, whether the labelled thyroid image is associated with one of the malignant thyroid nodule and the benign thyroid nodule,
wherein the analysis engine determines that the thyroid nodule of interest resembles the malignant thyroid nodule if the labelled thyroid image is associated with the malignant thyroid nodule and determines that the thyroid nodule of interest resembles the benign thyroid nodule if the labelled thyroid image is associated with the benign thyroid nodule.

7. The system of claim 1:
wherein the output report comprises additional data associated with the thyroid nodule of interest that is determined based on labels associated with the labelled thyroid image, the labels representing diagnostic data associated with the labelled thyroid image.

8. The system of claim 1, wherein to generate the machine learning model, the analysis engine is configured to train the machine learning algorithm using the plurality of labelled thyroid images as training data.

9. A non-transitory computer-readable medium comprising a plurality of instructions, which, when executed by an analysis engine of a computing device, causes the computing device to perform operations comprising:
generating, using a machine learning algorithm and a training dataset, a machine learning model that is configured to determine at least one labelled thyroid image that is similar to an ultrasound image of a thyroid nodule of interest,
wherein the machine learning algorithm comprises a multi-layer neural network algorithm that has been modified by removing a final fully connected classification layer,
wherein the training dataset comprises a plurality of labelled thyroid images, and wherein each labelled thyroid image comprises an ultrasound image of a thyroid nodule that has a confirmed diagnosis;

receiving an ultrasound image of a thyroid comprising the thyroid nodule of interest;

segmenting the ultrasound image of the thyroid to generate the ultrasound image of the thyroid nodule of interest;

processing, using the machine learning model, the ultrasound image of the thyroid nodule of interest to determine the at least one labelled thyroid image from the plurality of labelled thyroid images, the at least one labelled thyroid image being similar to the ultrasound image of the thyroid nodule of interest; and determining, based on the at least one labelled thyroid image, whether the thyroid nodule of interest is one of a malignant thyroid nodule and a benign thyroid nodule, wherein the at least one labelled thyroid image comprises multiple labelled thyroid images that have been determined by the machine learning model to be similar to the ultrasound image of the thyroid nodule of interest; and generating and display an output report that comprises:
(a) the multiple labelled thyroid images, and
(b) an identification of whether the thyroid nodule of interest resembles one of the malignant thyroid nodule and the benign thyroid nodule based on a labelled thyroid image of the multiple labelled thyroid images.

10. The non-transitory computer readable medium of claim 9, wherein determining the at least one labelled thyroid image that is similar to the ultrasound image of the thyroid nodule of interest comprises:

generating, using the machine learning model, a first feature vector associated with the ultrasound image of the thyroid nodule of interest; and for each of the plurality of labelled thyroid images, computing a similarity score that represents a similarity between the ultrasound image of the thyroid nodule of interest and the respective labelled thyroid image based on the first feature vector associated with the ultrasound image of the thyroid nodule of interest and a second feature vector associated with the respective labelled thyroid image.

11. The non-transitory computer readable medium of claim 10, wherein determining the at least one labelled thyroid image that is similar to the ultrasound image of the thyroid nodule of interest further comprises identifying the at least one labelled thyroid image that has a similarity score that is above a threshold similarity score; and outputting labels associated with the at least one labelled thyroid image.

12. The non-transitory computer readable medium of claim 10, wherein determining the at least one labelled thyroid image that is similar to the ultrasound image of the thyroid nodule of interest further comprises:

identifying the labelled thyroid images having top-N similarity scores; and outputting labels associated with the labelled thyroid images.

13. The non-transitory computer readable medium of claim 11, wherein the output report comprises additional data associated with the thyroid nodule of interest that is determined based on labels associated with the labelled thyroid image, the labels representing diagnostic data associated with the labelled thyroid image.

14. A computing device comprising:

an analysis engine that is configured to determine whether a thyroid nodule of interest is one a malignant thyroid nodule and a benign thyroid nodule, the analysis engine comprising:

a model generation module that generates, using a machine learning algorithm and a training dataset, a machine learning model that is configured to determine at least one labelled thyroid image that is similar to an ultrasound image of the thyroid nodule of interest, wherein the machine learning algorithm comprises a multi-layer neural network algorithm that has been modified by removing a final fully connected classification layer, wherein the training dataset comprises a plurality of labelled thyroid images, and wherein each labelled thyroid image comprises an ultrasound image of a thyroid nodule that has a confirmed diagnosis;

an image processing module that:

receives an ultrasound image of a thyroid comprising the thyroid nodule of interest;

segments the ultrasound image of the thyroid to generate the ultrasound image of the thyroid nodule of interest;

a model application module that processes, using the machine learning model, the ultrasound image of the thyroid nodule of interest to determine the at least one labelled 5 thyroid image from the plurality of labelled thyroid images, the at least one labelled thyroid image being similar to the ultrasound image of the thyroid nodule of interest; and an output generation module that determines, based on the at least one labelled thyroid image, whether the thyroid nodule of interest is one of the malignant thyroid nodule and the benign thyroid nodule, wherein the at least one labelled thyroid image comprises multiple labelled thyroid images that have been determined by the machine learning model to be similar to the ultrasound image of the thyroid nodule of interest; and the output generation module generates and displays an output report that comprises:
(a) the multiple labelled thyroid images, and
(b) an identification of whether the thyroid nodule of interest resembles one of the malignant thyroid nodule and the benign thyroid nodule based on a labelled thyroid image of the multiple labelled thyroid images.

15. The computing device of claim 14, wherein the ultrasound image of the thyroid is received from an external data source through at least one of a wireless and wired communication link.

16. The computing device of claim 14, wherein the ultrasound image of the thyroid is captured by an ultrasound imaging probe that is coupled to the computing device.

17. The computing device of claim 14, wherein to determine the at least one labelled thyroid image that is similar to the ultrasound image of the thyroid nodule of interest, the model application module is configured to:

generate, using the machine learning model, a first feature vector associated with the ultrasound image of the thyroid nodule of interest;

for each of the plurality of labelled thyroid images, compute a similarity score that represents a similarity between the ultrasound image of the thyroid nodule of interest and the respective labelled thyroid image based on the first feature vector associated with the ultrasound image of the thyroid nodule of interest and a second feature vector associated with the respective labelled thyroid image;

identify the at least one labelled thyroid image that has a similarity score that is above a threshold similarity score; and output labels associated with the at least one labelled thyroid image.

18. The computing device of claim 14, wherein the output report comprises additional data associated with the thyroid nodule of interest based that is determined based on labels associated with the labelled thyroid image, the labels representing diagnostic data associated with the labelled thyroid image.

\* \* \* \* \*